United States Patent
Fazan et al.

(10) Patent No.: US 9,427,492 B2
(45) Date of Patent: Aug. 30, 2016

(54) COMPOSITION CONTAINING INJECTABLE SELF-HARDENED APATITE CEMENT

(75) Inventors: Fazilah Binti Fazan, Shah Alam (MY); Salina Sabudin, Shah Alam (MY); Shirin Binti Ibrahim, Shah Alam (MY); Sudirman Bin Sahid, Shah Alam (MY); Wan Ruzaini Bin Wan Sulaiman, Shah Alam (MY); Nor Shahida Binti Kader Bashah, Shah Alam (MY)

(73) Assignee: SIRIM Berhad, Shah Alam (MY)

( * ) Notice: Subject to any disclaimer, the term of this patent is extended or adjusted under 35 U.S.C. 154(b) by 9 days.

(21) Appl. No.: 13/981,745

(22) PCT Filed: Sep. 29, 2011

(86) PCT No.: PCT/MY2011/000210
§ 371 (c)(1),
(2), (4) Date: Jul. 25, 2013

(87) PCT Pub. No.: WO2012/102601
PCT Pub. Date: Aug. 2, 2012

(65) Prior Publication Data
US 2013/0309214 A1 Nov. 21, 2013

(30) Foreign Application Priority Data
Jan. 27, 2011 (MY) .......................... PI2011000388

(51) Int. Cl.
*A61L 24/00* (2006.01)
*A61L 24/02* (2006.01)
*A61L 27/12* (2006.01)

(52) U.S. Cl.
CPC ........ *A61L 24/0063* (2013.01); *A61L 24/0015* (2013.01); *A61L 24/02* (2013.01); *A61L 27/12* (2013.01); *A61L 2400/06* (2013.01)

(58) Field of Classification Search
CPC .......................... A61L 24/0063; A61L 24/02
See application file for complete search history.

(56) References Cited

U.S. PATENT DOCUMENTS

2003/0021824 A1* 1/2003 Lacout et al. ................ 424/423
2010/0068243 A1* 3/2010 Khairoun et al. ............ 424/426

FOREIGN PATENT DOCUMENTS

EP  0 538 913 A1  4/1993

OTHER PUBLICATIONS

Huan et al.,"Effect of sodium carbonate on self-setting properties of tricalcium silicate bone cement", Journal of Biomaterials Applications, 2008, 23(3), abstract.*
Yokoyama et al., Development of calcium phosphate cement using chitosan and citric acid for bone substitute materials. Biomaterials. Feb. 2002;23(4):1091-101.

* cited by examiner

*Primary Examiner* — Laura Schuberg
(74) *Attorney, Agent, or Firm* — Wolf, Greenfield & Sacks, P.C.

(57) ABSTRACT

A method of producing an injectable calcium phosphate paste by a process in which calcium phosphate precursors are mixed with the setting fluids to form a self-hardened apatite cement is disclosed. The produced apatite cement is biocompatible, bioactive and biodegradable in the body. The pH value of said apatite cement is approximately 7 with compressive strength between 10-30 MPa and the setting process will not generate.temperature >37° C. The self-hardened apatite (SHA) cement is found to be bioresorbable and can be used for bone fillers, fixation of broken bones or artificial joints in human and also appropriate for use as a delivery vehicle.

18 Claims, 1 Drawing Sheet

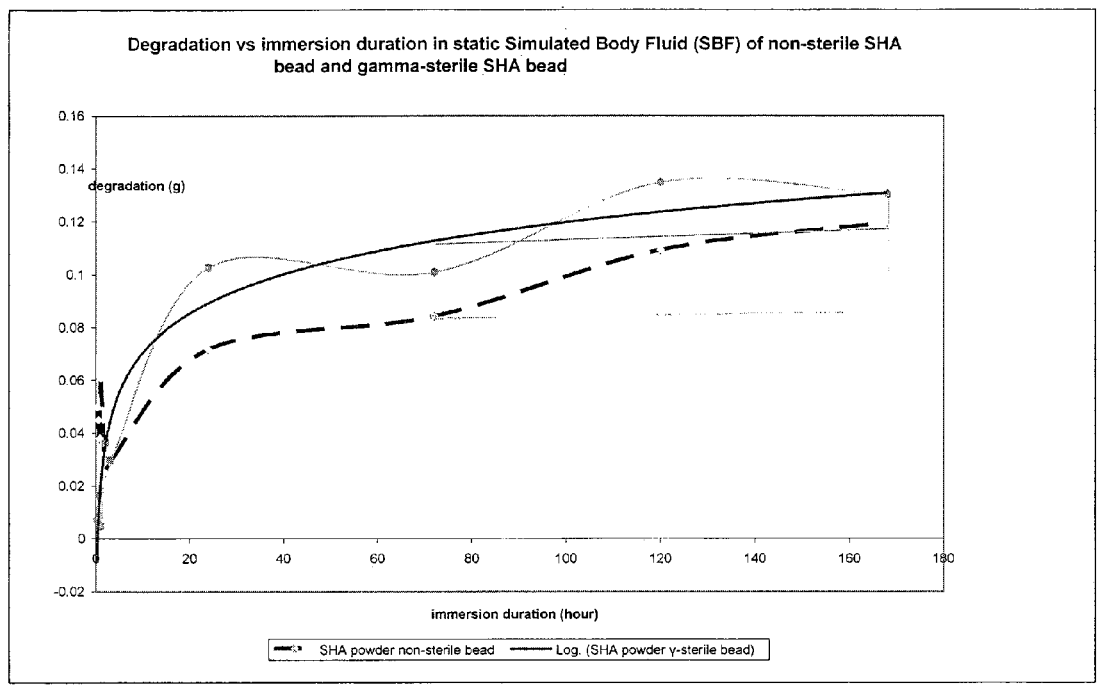

COMPOSITION CONTAINING INJECTABLE SELF-HARDENED APATITE CEMENT

RELATED APPLICATION

This application is a national stage filing under 35 U.S.C. §371 of international application PCT/MY2011/000210, filed Sep. 29, 2011 which was published under PCT Article 21(2) in English.

FIELD OF THE INVENTION

The present invention relates to bone cement composition. More particularly, the present invention relates to a bioresorbable self-hardened apatite (SHA) cement composition which is biocompatible, bioactive, and biodegradable in the body. The self-hardened apatite cement composition of the present invention is appropriate for fixation of broken bones or artificial joints, in humans, as bone fillers and can also be used as a delivery vehicle.

BACKGROUND OF THE INVENTION

Bone cements and calcium phosphate cements are the two major groups of cementing materials that are currently being used for the fixation of broken bones or artificial joints in human.

Bone cements are normally made from polymethyl-metacrylate (PMMA)—a polymer material, with ceramics filler, for example zirconium oxide or barium sulphate. It is used for fixation of artificial joints to the skeleton. Basically, the bone cements are two-component materials, i.e. consists of pre-polymerized PMMA plus fillers in the form of a powder, and another is a monomer liquid. There are many drawbacks to these bone cements, such as polymerization which develops temporary heat between 60° C. to 100° C. that is found detrimental to the surrounding tissues, as cells cannot survive temperatures over 47° C. Bone cements are brittle and prone to fatigue failure. They are mechanically weak when they entrap impurities such as air and blood. They produce "wear debris" that can cause osteolysis (i.e., bone resorption). Bone cements may support colonisation of bacteria and development of post-operative infections. They may also cause allergy and anaphylactic reaction during surgery.

Calcium phosphate (CaP) cements consists of calcium phosphate precursors mixed with a setting solution to form calcium phosphate paste or dough that eventually hardened into solid material. There are various combinations of calcium phosphate precursors, such as $CaHPO_4.2H_2O$, $CaHPO_4$, $Ca_2P_2O_7$, $Ca_2H_2P_2O_8$, etc. Some of the powder mixtures may need to be heated to temperatures up to 1000° C. before mixing with the setting solution. The setting solutions could be in turns of basic aqueous solutions, acidic aqueous solutions, solvents or water. Other than these calcium phosphate precursors, fillers (e.g. MgO, strontium, collagen), accelerator agents (e.g. LiCl, LiOH), retarder agents (e.g. polysaccharide, glycerine, starch) and pH controlling agents (e.g. HCl, $HNO_3$, $NH_3O_4$, $Na_2HPO_4$, etc.,) were also used.

There are few drawbacks to CaP cements, such as hardening reaction temperatures ranging between 30-150° C. For temperatures exceeding 45° C., these are detrimental to the surrounding tissues since cells cannot survive temperatures over 47° C. The pH of the CaP cements ranges between acidic to highly basic (pH ~5-12). In micro-environment, these could be detrimental causing irritation and inflammatory reactions to the surrounding cells which requires pH ~7 for the body homeostasis. Thus, it may take a very long time to reach neutral pH. Usage of complex chemicals may also affect the biocompatibility properties of the CaP cements, apart from it being more difficult or more expensive to produce. Some of the cements take very long time to degrade. Controlled degradation is favorable so that the body can have time to replace the synthetic materials with the host bone. Too fast or too slow resorption is both unfavourable. Therefore there is a need for an invention that can achieve one or more of the following objectives which constitutes the objectives of the present invention i.e.

1. To produce a self-hardened apatite (SHA) cement which is biodegradable, biocompatible and bioactive in the body, as well as to enhance bone growth and bone integration;
2. To produce a self-hardened apatite (SHA) cement which has neutral pH (~7);
3. To produce a self-hardened apatite (SHA) cement which has compressive strength of between 10-30 MPa, which is suitable for both non-load bearing and some load bearing applications;
4. The hardening or setting process of the cement composition should not generate heat greater than 37° C., which is the normal body temperature; and
5. The self-hardened apatite cement is also suitable to be used as a delivery vehicle.

SUMMARY OF THE INVENTION

Accordingly, the first aspect of the present invention provides for a composition of an injectable self-hardened apatite (SHA) cement comprising:

a. a main matrix comprising tri-calcium phosphate (TCP; $Ca_3(PO_4)_2$) and tetra-calcium phosphate (TTCP; $Ca_4(PO_4)_2O$),
b. hardening agents comprising sodium carbonate ($Na_2CO_3$), citric acid ($C_6H_8O_7$) and sodium citrate ($C_6H_5Na_3O_7.2H_2O$),
c. setting fluids and
d. filler and pH stabiliser.

The second aspect of the present invention is that the resultant injectable self-hardened apatite cement has a neutral pH of approximately 7 and is biocompatible, bioactive, biodegradable in the human body.

The third aspect of the present invention is that the injectable self-hardened apatite cement has compressive strength of between 10-30 MPa and will not generate temperature greater than 37° C. during the setting process.

The composition of the present invention will now be described in detail below:

BRIEF DESCRIPTION OF THE DRAWING

FIG. 1 is a plot showing degradation or weight loss of non-sterile and gamma-sterilized self-hardened apatite (SHA) beads over time during which they were immersed in a static simulated body fluid (SBF).

DESCRIPTION OF THE PREFERRED EMBODIMENT

Preparing the Self-Hardened Apatite Cement

Self-harden apatite cement (SHA) were prepared using TCP+TTCP as a main matrix and mixed with sodium carbonate, citric acid, sodium citrate and Hydroxyapatite. TTCP+TCP were ground at 0.1 MPa (1 bar) for 1 minute using mortar grinder machine, while other precursors were manually ground for 2 minutes. These precursors were further mixed with 2 g of double-distilled deionized water (DDI) as a setting solution using spatula and weighing boat. The slurry was moulded into spherical Perspex mould at 37° C. in an oven (Binder FD115, USA) for approximately 6 hours. This will produce solid spherical beads with diameter approximately 8 mm.

The percentage of each chemical used in the preparation of the injectable self-hardened apatite cement is listed in Table 1 below.

TABLE 1

Percentage of each chemical in the self-hardened apatite

| Chemicals | Weight (g) | Weight (%) | Weight (%) range |
|---|---|---|---|
| TCP + TTCP | 2 g | 55% | 45:55-55:45 |
| Sodium carbonate | 0.318 g | 8.74% | 5-10 |
| Citric acid | 0.961 g | 26.42% | 20-35 |
| Sodium citrate | 0.258 g | 7.09% | 5-10 |
| Hydroxyapatite | 0.1 g | 2.75% | 1-5 |

A comparative study on the TCP:TTCP weight ratio was also carried out and the results are shown in Table 2 below.

TABLE 2

| Sample | TCP | TTCP | TCP:TTCP |
|---|---|---|---|
| 1 | 0.0713 g 47% | 0.0795 g 53% | 47%:53% |
| 2 | 0.058 g 51% | 0.0555 g 49% | 51%:49% |
| 3 | 0.0595 g 42% | 0.0821 g 58% | 42%:58% |
| 4 | 0.0477 g 46% | 0.0565 g 54% | 46%:54% |
| 5 | 0.088 g 54% | 0.074 g 46% | 54%:46% |

The samples were evaluated and it was found that the TCP:TTCP of 45:55 to 55:45 ratios produce workable SHA; which falls within the required objectives. Furthermore, the hardening or setting process did not generate heat greater than 37° C., which is the body temperature. Therefore, the SHA cement can also be used as a delivery vehicle to deliver selected material, especially those that are heat-sensitive such as drugs, proteins and plasma, to the human body.

Study on the DDI Effect

After the composition has been prepared, a study on the DDI effect was carried out and the results are shown in Table 3 below:

TABLE 3

Study on DDI effect and determination of workable DDI range:

| | A 1.5 ml | B 2 ml (original formulation) | C 2.5 ml | D 3 ml | E 3.5 ml | F 4 ml | G 6 ml | H 8 ml | I 10 ml |
|---|---|---|---|---|---|---|---|---|---|
| Bubbles released | Can't get rid of bubbles | 1"30 s-2" | 1"30 s-2" | 1"30 s | Less bubbles | <E | <F | <G | <H |
| Mixing | mixing not complete | 0-2" | 0-3" | 0-4" | 0-4" | 0-9" | 0-13" | 0-17" | 0-25" |
| Moulding/ injectable ability | Not enough time | 2"-4" | 3"-4" | 4" | 4" | 9" | 13" | 17" | 25" |
| Start hardening | 1" | 3"-5" | 5" | 5" | 5" | 11" | 16" | 21" | 29" |
| Complete hardening | 10" | 13"-15" | 13"-15" | 1 hour | 1 hour | 1'30" | 3 hours | 4 hours | 4 hours |
| Observation after 15" (oven) | — | Complete harden | Complete harden | Not complete harden, press → flattened | Not complete harden, press → flattened | Not complete harden, press → flattened | Not complete harden, press → flattened | Not complete harden, press → flattened | Not complete harden, press → flattened |
| Observation after complete hardening | Hard to break (A > B), rough surface | CS: 25.1 MPa | C = B | Hard but brittle | Hard but brittle | Hard but brittle, smooth surface | Hard but brittle, smooth surface | Hard but brittle, rough surface | Hard but brittle, rough surface |

In the present invention, the TCP and TTCP form the main matrix, whereas sodium carbonate, citric acid and sodium citrate are the hardening agents and the hydroxyapatite ($Ca_{10}(PO_4)_6(OH)_2$) is used as a filler and as a pH stabiliser. The setting fluids used in the present composition are selected from a group of pure water, saline solution, body fluids such as body electrolyte, blood plasma or whole blood, solutions of drugs, proteins and hormones.

From the above study, it was found that the amount of DDI water between 1.5-3 ml for the given chemical powder compositions as in Table 1 produces SHA. The use of less or more DDI water than the values described in Table 3 above produces soft to pasty samples that would not harden at all within 30 minutes and hence are not useful as injectable in bone cement applications. The working time prior to injectable occurs when all bubbles has been released is between 2-5 minutes under atmospheric conditions. These are the times that the slurry slowly turns into injectable paste form. The complete hardening or setting process to produce said SHA cement occurs between 13-15 minutes in a physiologic environment at 37° C. Thus the preferred embodiment according to the study conducted is 2 ml (~2 g) DDI water.

Study on the Different Setting Fluids

The setting fluids used in the present composition are selected from a group of pure water, saline solution, body fluids such as body electrolyte, blood plasma or whole blood, solutions of drugs, proteins and hormones. Examples of the different setting fluids on the SHA cements prepared are shown in the Table 4 below:

TABLE 4

Observation on the different setting fluids used

| Setting fluid | Pure DDI water | Saline solution | Body electrolytes |
|---|---|---|---|
| Setting time: | | | |
| Bubbles released | 1.5 minutes-2 minutes | 1.5 minutes | 1 minute |
| Mixing | 0-2 minutes | 0-3 minutes | 0-3 minutes |
| Moulding | 2 minutes-4 minutes | 3-4 minutes | 3.5 minutes-4 minutes |
| Hardening time: | | | |
| Starts hardening | 3 minutes-5 minutes | 5 minutes | 4-7 minutes |
| Hardened | 13 minutes-15 minutes | 10-15 minutes | 12-16 minutes |
| Observation of the sample | Complete harden after 15 minutes in oven (37° C.) Hard to break | Complete harden after 30 minutes in oven (37° C.) Hard to break | Complete harden after 30 minutes in oven (37° C.) Hard to break |
| Strength | 10-25 MPa | | |

From the above study, it was found that despite different setting fluids used with the chemical powder composition as in Table 1, the SHA produced gave similar working and hardening times. The slurry which turns into paste form is suitable for injectable applications. However the presence of electrolytes and/or other compositions such as proteins, hormones, drugs, etc, may increase the completion of hardening process in the physiologic environment at 37° C. from 15 to 30 minutes.

Study of the Heat Released During Setting Process

The hardening or setting process of the cement composition is expected not to generate heat greater than 37° C.; which is the normal body temperature. Thus the study was conducted to evaluate the heat generated during the setting process, and the results are listed in the Table 5 below.

TABLE 5

Heat generated during setting process of SHA cement

| Batch No. | Recorded Temperature (Heat Generated during setting process) |
|---|---|
| F1 | 28.0° C. ± 0.1° C. |
| F2 | 32.0° C. ± 0.5° C. |
| F3 | 28.0° C. ± 0.1° C. |
| F4 | 29.0° C. ± 0.5° C. |
| F5 | 29.0° C. ± 0.1° C. |
| F6 | 28.0° C. ± 0.1° C. |
| F7 | 28.0° C. ± 0.1° C. |
| F8 | 25.5° C. ± 0.7° C. |
| F9 | 29.0° C. ± 0.1° C. |
| F10 | 28.0° C. ± 0.5° C. |

As shown in the Table 5 above, the heat generated during the setting process is less than 37° C., thus it had achieved the targeted objective. Since the heat generated does not exceed 37° C., the SHA cement will able to embody temperature sensitive additives such as drugs, proteins, hormones, etc. The less than 37° C. heat generated during hardening process will also enable the injectable SHA cement to be safely hardened and used in the human body. If the cements hardening temperatures exceed 45° C., it will denature proteins, hormones and other temperature sensitive drugs. Not only it would not be able to carry these additives, the hardening process of the cements will also be detrimental to the surrounding tissues since cells cannot survive temperatures over 47° C.

pH Value of SHA Bead in Simulated Body Fluids (SBF)

The pH value of the hardened product is neutral (pH ~7) under fluid environment, similar to body pH. The SHA bead was immersed in Simulated Body Fluid (SBF) and it was found that the pH values were maintained in neutral condition even at day 7 of immersion. The results of this experiment are tabulated in Table 6 below.

TABLE 6 pH value of SHA bead in SBF

| Immersion duration (hour) in Simulated Body Fluid (SBF) | pH value of SHA bead in SBF |
|---|---|
| 0.25 | 7.40 ± 0.02 |
| 0.5 | 7.39 ± 0.03 |
| 0.75 | 7.39 ± 0.06 |
| 1 | 7.36 ± 0.06 |
| 2 | 7.34 ± 0.02 |
| 3 | 7.30 ± 0.06 |
| 24 (1 day) | 7.28 ± 0.04 |
| 72 (3 days) | 7.25 ± 0.04 |
| 120 (5 days) | 7.23 ± 0.03 |
| 168 (7 days) | 7.17 ± 0.03 |

Further, SHA beads (0.4 g) will degrade at the rate of 45 days (±2 days). This property constitutes for its bioresorbability and thus can be used as delivery vehicle applications.

Study on Compression Strength Range

The compression strength ranges of the different combinations of the chemicals are listed in Table 7 below. From the table, it can be found that the compression strength typically ranges between 10 MPa (100 bar) and 30 MPa (300 bar), thus suitable for both non-load bearing and some load bearing applications. Lower MPa products are used as delivery vehicle and non-load bearing bone cavity filler especially for osteoporotic bone, while higher MPa products are used as injectable bone cements for prosthetic fixation.

TABLE 7

Compression strength range

| No | TTCP + TCP | Sodium carbonate | Citric acid | Sodium citrate | Hydroxyapatite | DDI | CS (MPa) |
|---|---|---|---|---|---|---|---|
| 1 | 2 g | 0.318 g | 0.961 g | 0.258 g | 0.1 g | 2 g | 25.1 ± 2.2 |
| 2 | 2 g | 0.318 g | 0.961 g | 0.516 g | 0.1 g | 2 g | 14.97 + 3.44 |
| 3 | 2 g | 0.318 g | 0.961 g | 0.774 g | 0.1 g | 2 g | 10.2 + 1.36 |
| 4 | 2 g | 0.318 g | 1.14 g | 0.258 g | 0.2 g | 2 g | 19.41 + 3.45 |
| 5 | 2 g | 0.53 g | 0.961 g | — | — | 2 g | 9.51 + 1.45 |
| 6 | 2 g | 0.318 g | 0.961 g | — | — | 2 g | 22.68 + 4.65 |
| 7 | 2 g | 0.318 g | 0.769 g | — | — | 2 g | 14.41 + 1.96 |
| 8 | 2 g | — | 0.38 g | 0.88 g | — | 2 g | 2.37 |

Properties of the Final Product

Self-harden apatite cement (SHA) were prepared using TTCP+TCP (2 g) as a main matrix and mixed with sodium carbonate (0.318 g), citric acid (0.961 g), sodium citrate (0.258 g) and Hydroxyapatite (0.1 g). TTCP+TCP were ground at 0.1 MPa (1 bar) for 1 minute using mortar grinder machine, while other precursors were manually ground for 2 minutes. These precursors were further mixed with 2 g of double-distilled deionized water (DDI) as a setting solution using spatula and weighing boat.

The mixing process will take about 2 minutes. Bubbles will release in about 1.5-2 minutes. After all the bubbles have been released, the slurry is ready for moulding at 2-4 minutes. The slurry starts to harden at 3-5 minutes and is completely hardened at 13-15 minutes. Initial pH and temperature is 7.13 and 28° C. respectively.

If the slurry were moulded, poured or injected into a cylindrical shape teflon mould (Ø~6 mm, height~12 mm), the physical properties of SHA as follows will be obtained:—Height: 12 mm (±0.05 mm), diameter: 5.92 mm (±0.04=), weight: 0.54 g (±0.01 g), apparent density: 1.62 g/cm$^3$ (±0.02 g/cm$^3$), true density: 3.4069 g/cm$^3$ (±0.34 g/cm$^3$) and total porosity: 56%. The porosity value may enable the SHA cement to contain additives such as drugs, proteins, hormones, etc as a delivery vehicle. Furthermore, the compressive strength of SHA cement of between ~10-25 MPa (100-250 bar) is suitable for both non-load bearing and some load bearing applications. Thus the applications for this SHA cement ranges from as a delivery vehicle to injectable non-load bearing bone fillers and to some load-bearing prosthetic fixations.

Study on the Degradation Property

Two sets of SHA samples were prepared for the degradation study. One set was non-sterile SHA while another set was gamma γ-sterile SHA at 25kGy irradiation. SHA bead was then immersed in 30 ml of simulated body fluid (SBF) at 37° C. using Incubator (Memmert BE 600, Germany) for various immersion times (1 day, 3 days, 5 days and 7 days). The SBF with ion concentrations equivalent to human blood plasma was freshly prepared by dissolving reagent-grade chemicals of NaCl, NaHCO$_3$, KCl, K$_2$HPO$_4$.3H$_2$O, MgCl$_2$.6H$_2$O, CaCl$_2$ and Na$_2$SO$_4$ in DDI water. The solution was buffered at pH 7.4 with 1M HCl and tris (hydroxymethyl) aminomethane at 37° C. The comparative amounts of ionic concentrations in mM of SBF and human blood plasma are listed in Table 8.

TABLE 8

Ion concentrations of SBF and human blood plasma

| | Ion concentration (mM) | | | | | | | |
|---|---|---|---|---|---|---|---|---|
| | Na$^+$ | K$^+$ | Mg$^{2+}$ | Ca$^{2+}$ | Cl$^-$ | HCO$_3^-$ | HPO$_4^{2-}$ | SO$_4^{2-}$ |
| SBF solution | 142.0 | 5.0 | 1.5 | 2.5 | 148.8 | 4.2 | 1.0 | 0 |
| Human blood plasma | 142.0 | 5.0 | 1.5 | 2.5 | 103.0 | 27.0 | 1.0 | 0.5 |

SHA were removed from SBF and dried at room temperature after complete immersion. Studies of degradation were calculated by weighing the SHA weight before and after immersion. The plot for the degradation or weight loss of the SHA beads over time (hours) up to 7 days period is shown in FIG. 1.

Study that has been conducted shows that gamma γ-sterilized self-hardened apatite (SHA) cement bead with a weight of 0.4 g will degrade 0.13 g after 7 days immersion in SBF solution. It can be estimated that the SHA will completely degrade after 54 days immersion in SBF. The calculation as follows:

$$\text{Degradation rate} = 0.13047 - 0.1008/(7-3) \text{ day}$$
$$= 0.02967/4 \text{ day}$$
$$= 7.42 \times 10^{-3}$$

1 bead (0.4 g), will degrade in 0.4 g/7.42 × 10$^{-3}$ = 54 days (±1 day)

Meanwhile, non-sterilized SHA cement bead with a weight of 0.4 g will degrade 0.12 g after 7 days immersion in SBF solution and completely degrade after 45 days immersion in SBF solution.

$$\text{Degradation rate} = 0.11966 - 0.08424/(7-3) \text{day}$$
$$= 0.03536/4 \text{ day}$$
$$= 8.84 \times 10^{-3}$$

1 bead (0.4 g), will degrade in 0.4 g/8.84 × 10$^{-3}$ = 45 days (±2 days)

Thus the gamma sterilized SHA cement may take slightly longer time to completely degrade in the body compared to the non-sterile SHA cement.

Table 9 below lists the formulation, chemical, physical and mechanical properties of the final product prepared according to the present invention.

TABLE 9

Properties of the final product

| | |
|---|---|
| Code | F4 |
| Raw material & Formulation | TTCP + TCP (2 g) + sodium carbonate (0.318 g) + citric acid (0.961 g) + sodium citrate (0.258 g) + Hydroxyapatite (0.1 g) + DDI (2 g) |

TABLE 9-continued

Properties of the final product

| | |
|---|---|
| Process | TTCP + TCP were ground at 1 bar for 1 minute, while other precursors for 2 minutes<br>Mix all precursors with DDI using spatula & weighing boat<br>Slurry is ready for moulding after all bubbles were released |
| Working & hardening time | Bubbles released: 1.5 minutes-2 minutes<br>Mixing: 0-2 minutes<br>Moulding: 2 minutes-4 minutes<br>Start hardening: 3 minutes-5 minutes<br>Hardened: 13 minutes-15 minutes |
| Chemical properties: pH, temperature | pH: 7.13<br>T: 28° C. |
| Physical properties | Height: 12 mm ± 0.05<br>Diameter: 5.92 mm ± 0.04<br>Weight: 0.54 g ± 0.01<br>Apparent density: 1.62 g/cm$^3$ ± 0.02<br>True density: 3.4069 g/cm$^3$ ± 0.34<br>Total porosity: 56% |
| Mechanical property | CS: 10-25 MPa (100-250 bar) |
| Degradation study | Complete degrade after 50 days |

It is well known that both TCP and TTCP are biodegradable and biocompatible, and in the host body in many clinical studies they have been shown to have bioresorbable and bioactive properties; whereby the dissolved TCP and TTCP were later replaced by the human bone.

While the invention has been described in connection with certain preferred embodiments illustrated above, it will be understood that it is not intended to limit the invention to these particular embodiments. On contrary, it is intended to cover all alternatives, modifications and equivalents as may be included within the scope of the invention as defined, by the appended claims.

What is claimed is:

1. A composition of injectable self-hardened apatite cement comprising:
    a. a main matrix comprising tri-calcium phosphate (TCP; $Ca_3(PO_4)_2$) and tetra-calcium phosphate (TTCP; $Ca_4(PO_4)_2O$),
    b. hardening agents comprising sodium carbonate ($Na_2CO_3$), citric acid ($C_6H_8O_7$) and sodium citrate ($C_6H_5Na_3O_7.2H_2O$),
        wherein said sodium carbonate is present in an amount ranging from about 5 to 10 weight percentage,
        wherein said citric acid is present in an amount ranging from about 20 to 30 weight percentage, and,
        wherein said sodium citrate is present in an amount ranging from about 5 to 10 weight percentage, and
    c. filler and pH stabilizer.

2. The composition according to claim 1 wherein the filler and pH stabiliser is hydroxyapatite ($Ca_{10}(PO_4)_6(OH)_2$).

3. The composition according to claim 1, wherein a weight ratio of tri-calcium phosphate to tetra-calcium phosphate is in the range of 45:55 to 55:45.

4. The composition according to claim 1, wherein said filler and/or pH stabiliser is present in an amount ranging from about 1 to 5 weight percentage.

5. The composition according to claim 1, wherein a hardening or setting process to produce said self-hardened apatite generates heat lesser than 37° C. in an in vitro environment.

6. The composition according to claim 1, wherein a working time prior to injectable occurs when all bubbles has been released between 2 to 5 minutes under atmospheric conditions.

7. The composition according to claim 1, wherein a complete hardening or setting process to produce said self-hardened apatite cement occurs between 13 to 30 minutes in a physiologic environment depending on a setting fluids used.

8. The composition according to claim 1, wherein a pH value of the self-hardened apatite is neutral, in the range of 7.0 to 7.5 under body fluid environment.

9. The composition according to claim 1, wherein the self-hardened apatite cement is bioactive.

10. The composition according to claim 1, wherein the self-hardened apatite cement is biocompatible to human body that enhances bone growth and bone integration.

11. The composition according to claim 1, wherein the self-hardened apatite cement is biodegradable in the human body facilitating replacement by host bone.

12. The composition according to claim 1, wherein the self-hardened apatite cement has a compressive strength of between 10-30 MPa (100-300 bar) that is suitable for non-load bearing and some load bearing applications.

13. The composition according to claim 1, wherein the self-hardened apatite cement is an injectable calcium phosphate cement and can be injectable into patient bone cavity.

14. The composition according to claim 1, wherein the injectable self-hardened apatite cement can be used as a delivery vehicle by adding any temperature-sensitive drugs, proteins, plasma rich platelets and growth hormones.

15. The composition according to claim 1, further comprising a setting fluid.

16. The composition according to claim 15, wherein the setting fluid is selected from a group consisting of pure water, saline solution, body fluids body electrolyte, blood plasma whole blood, solutions of drugs, solutions of proteins, and solutions of hormones.

17. A composition of injectable self-hardened apatite cement comprising,
    a. 2 g of tetra-calcium phosphate and tri-calcium phosphate mixture,
    b. 0.318 g of sodium carbonate,
    c. 0.961 g of citric acid,
    d. 0.258 g of sodium citrate, and
    e. 0.1 g of hydroxyapatite acting as a filler and a pH stabiliser.

18. The composition according to claim 17 for use as injectable self-hardened apatite cement injectable into patient bone cavity.

\* \* \* \* \*